United States Patent
Hoyer et al.

(10) Patent No.: US 8,852,950 B2
(45) Date of Patent: Oct. 7, 2014

(54) METHOD AND DEVICE FOR MEASURING $NO_x$ CONCENTRATION USING MEASUREMENTS OF $NO_x$ AND A SECOND GAS COMPONENT

(75) Inventors: Knut Hoyer, Schwenningen (DE); Andreas Kaufmann, Kirchzarten (DE); Reinhold Munch, Freiburg (DE); Thomas Springmann, Kirchzarten (DE)

(73) Assignee: Testo AG, Lenzkirch (DE)

( * ) Notice: Subject to any disclaimer, the term of this patent is extended or adjusted under 35 U.S.C. 154(b) by 538 days.

(21) Appl. No.: 13/062,068

(22) PCT Filed: Sep. 3, 2008

(86) PCT No.: PCT/EP2008/007190
§ 371 (c)(1),
(2), (4) Date: Mar. 3, 2011

(87) PCT Pub. No.: WO2010/025745
PCT Pub. Date: Mar. 11, 2010

(65) Prior Publication Data
US 2011/0165692 A1 Jul. 7, 2011

(51) Int. Cl.
*G01N 33/00* (2006.01)
*G01N 21/76* (2006.01)
*G01N 27/10* (2006.01)
*G01N 27/27* (2006.01)
*G01N 27/407* (2006.01)
*G01N 27/417* (2006.01)

(52) U.S. Cl.
CPC .................................. *G01N 33/0037* (2013.01)
USPC ............... 436/118; 204/424; 422/52; 422/93; 422/98; 436/116; 436/117; 436/136; 436/149; 436/151; 436/172

(58) Field of Classification Search
USPC .......... 422/52, 83, 93, 98; 436/116–118, 172, 436/136, 149, 151; 204/424
See application file for complete search history.

(56) References Cited

U.S. PATENT DOCUMENTS 3,909,204 A * 9/1975 Allen ............................... 422/90
3,967,933 A * 7/1976 Etess et al. ..................... 436/118
3,979,589 A 9/1976 Sternberg et al.
(Continued)

FOREIGN PATENT DOCUMENTS

DE 19631002 7/1998
EP 1715338 10/2006

OTHER PUBLICATIONS

Black, F. M. et al, Environmental Science & Technology 1974, 8, 149-152.*

(Continued)

*Primary Examiner* — Arlen Soderquist
(74) *Attorney, Agent, or Firm* — Volpe and Koenig, P.C.

(57) ABSTRACT

A method for determining an $NO_x$ concentration in a measurement gas is provided, where a measurement value for the $NO_x$ concentration is determined from the sensor signal of a gas sensor and a measurement value for the concentration of a second component in the measurement gas is determined. A corrected value for the $NO_x$ in the measurement gas is determined from the measurement values, and the measurement value and the corrected measurement value for the $NO_x$ concentration are displayed and/or output.

21 Claims, 3 Drawing Sheets

(56) References Cited

U.S. PATENT DOCUMENTS

| | | | | |
|---|---|---|---|---|
| 3,996,005 | A * | 12/1976 | Topol | 436/117 |
| 4,141,800 | A * | 2/1979 | Breuer et al. | 205/779.5 |
| 4,236,895 | A * | 12/1980 | Stahl | 436/116 |
| 4,272,249 | A * | 6/1981 | D'Antonio | 436/136 |
| 4,315,753 | A * | 2/1982 | Bruckenstein et al. | 436/118 |
| 4,335,073 | A * | 6/1982 | Sherwood et al. | 422/83 |
| 4,560,873 | A | 12/1985 | McGowan et al. | |
| 4,822,564 | A * | 4/1989 | Howard | 422/52 |
| 4,829,183 | A | 5/1989 | McClatchie et al. | |
| 5,240,486 | A * | 8/1993 | Springmann et al. | 55/320 |
| 5,314,828 | A * | 5/1994 | Dalla Betta et al. | 436/118 |
| 5,341,643 | A * | 8/1994 | Hamburg et al. | 60/276 |
| 5,358,874 | A * | 10/1994 | Tsurumi | 436/116 |
| 5,418,366 | A | 5/1995 | Rubin et al. | |
| 5,569,838 | A * | 10/1996 | Broedel et al. | 73/23.31 |
| 5,624,640 | A * | 4/1997 | Potthast et al. | 422/90 |
| 5,633,170 | A * | 5/1997 | Neti | 436/116 |
| 5,705,129 | A * | 1/1998 | Takahashi et al. | 422/90 |
| 5,733,436 | A * | 3/1998 | Demisch et al. | 205/775 |
| 5,800,783 | A * | 9/1998 | Nanaumi et al. | 422/94 |
| 5,846,831 | A * | 12/1998 | Silvis | 436/55 |
| 5,847,263 | A * | 12/1998 | Springmann et al. | 73/29.01 |
| 5,872,305 | A * | 2/1999 | Springmann | 73/23.31 |
| 5,873,252 | A * | 2/1999 | Springmann | 62/3.4 |
| 5,942,190 | A * | 8/1999 | Kato et al. | 422/98 |
| 5,976,889 | A * | 11/1999 | Hirai et al. | 436/116 |
| 6,022,510 | A * | 2/2000 | Springmann | 422/534 |
| 6,044,689 | A * | 4/2000 | Yoshida et al. | 73/31.03 |
| 6,062,064 | A * | 5/2000 | Yoshida et al. | 73/23.2 |
| 6,126,902 | A * | 10/2000 | Kunimoto et al. | 422/94 |
| 6,174,421 | B1 | 1/2001 | Schumann | |
| 6,214,207 | B1 * | 4/2001 | Miyata et al. | 205/781 |
| 6,214,208 | B1 * | 4/2001 | Ando et al. | 205/781 |
| 6,295,862 | B1 * | 10/2001 | Kurokawa et al. | 73/31.05 |
| 6,319,377 | B1 | 11/2001 | Hasei et al. | |
| 6,375,828 | B2 * | 4/2002 | Ando et al. | 205/781 |
| 6,401,522 | B1 * | 6/2002 | Kon et al. | 73/31.05 |
| 6,635,161 | B2 * | 10/2003 | Inagaki | 204/425 |
| 6,773,565 | B2 * | 8/2004 | Kunimoto et al. | 204/425 |
| 6,780,378 | B2 * | 8/2004 | Abbasi et al. | 422/78 |
| 6,787,014 | B2 * | 9/2004 | Hasei et al. | 204/424 |
| 6,839,238 | B2 * | 1/2005 | Derr et al. | 361/735 |
| 6,878,339 | B2 * | 4/2005 | Akiyama et al. | 422/62 |
| 6,922,639 | B2 * | 7/2005 | Kawase et al. | 702/24 |
| 7,013,700 | B2 * | 3/2006 | Rombach | 73/1.06 |
| 7,029,920 | B2 * | 4/2006 | Lanier et al. | 436/116 |
| 7,297,549 | B2 * | 11/2007 | Lanier et al. | 436/175 |
| 7,321,287 | B2 * | 1/2008 | Ota et al. | 338/25 |
| 7,442,555 | B2 * | 10/2008 | Nair et al. | 436/113 |
| 7,469,531 | B2 * | 12/2008 | Viola | 60/286 |
| 7,771,654 | B1 * | 8/2010 | Moore et al. | 422/62 |
| 7,846,739 | B2 * | 12/2010 | von Bahr et al. | 436/116 |
| 8,177,957 | B2 * | 5/2012 | Martin | 205/781 |
| 8,527,179 | B2 * | 9/2013 | Tabares et al. | 701/101 |
| 2002/0106306 | A1 * | 8/2002 | Wang et al. | 422/98 |
| 2002/0106307 | A1 * | 8/2002 | Clyde et al. | 422/98 |
| 2003/0082821 | A1 * | 5/2003 | Lanier et al. | 436/118 |
| 2004/0072360 | A1 * | 4/2004 | Naaman et al. | 436/116 |
| 2004/0241868 | A1 * | 12/2004 | Cox et al. | 436/116 |
| 2005/0191754 | A1 * | 9/2005 | Audouin et al. | 436/116 |
| 2006/0223190 | A1 * | 10/2006 | Nakamura | 436/116 |
| 2011/0016948 | A1 * | 1/2011 | Tabares et al. | 73/23.31 |

OTHER PUBLICATIONS

Black, F. M. et al, Environmental Science & Technology 1974, 8, 149-152.*

Langmaier, J. et al, Sensor & Actuators B 1997, 41, 1-6.*

Yang, J.-C. et al, Sensors & Actuators B 2007, 125, 30-39.*

Glatz, Peter, SGA—Bulletin, No. 27, Sep., Oct., Nov. 1999, "Very Low Level NO/Nox Measurement".

* cited by examiner

METHOD AND DEVICE FOR MEASURING $NO_x$ CONCENTRATION USING MEASUREMENTS OF $NO_x$ AND A SECOND GAS COMPONENT

BACKGROUND

The invention relates to a method for determining a $NO_x$ concentration in a measurement gas, wherein a sensor signal of a gas sensor that is sensitive for $NO_x$ and is brought into contact with the measurement gas is captured and a measurement value for the $NO_x$ concentration is determined from the sensor signal, and to a device for carrying out this method.

Such methods are already known, wherein chemiluminescence detectors (CLD) are preferably used as the gas sensors. For example, such methods are used for testing legal limit values, for example, for determining the specific nitrogen oxide emission as an exhaust gas characteristic of a combustion engine, but these methods are also used in other applications.

Legal limit values for nitrogen oxide content in a measurement gas, for example, the exhaust gas of a combustion engine, have often been established for reasons of climate protection or for other political reasons, wherein sanctions can be imposed for non-compliance. Such regulations often refer to a specifically predetermined measurement method, in order to rule out legal uncertainties.

SUMMARY

The invention is based on the objective of creating an improved method for determining a $NO_x$ concentration in a measurement gas that is suitable for inspecting the compliance of legal or other regulations.

For meeting this objective, in a method of the type noted above it is provided that a measurement value is determined for the concentration of a second component in the measurement gas and that a numerical value for the $NO_x$ concentration in the measurement gas is determined from the measurement value for the concentration of the second component in the measurement gas. The method according to the invention offers the advantage that by determining the concentration of a second component in the measurement gas, a legally specified gas sensor, and thus a legally specified measurement method or a gas sensor type established as a reference or an established reference measurement method can be simulated or systematic measurement errors of a specified measurement method can be corrected for other measurements, wherein the usability of the method being applied for conclusions on the compliance of a specified limit value or for the comparison with other numerical values is not negatively affected or is enabled. The method according to the invention could also be used advantageously for engine settings for which a technician should use a comparable measurement device that allows a comparison with measurement values recorded in other ways or with other measurement methods.

According to one construction of the invention, it could be provided that the second component is oxygen. Tests have shown that for the frequently used chemiluminescence detectors, a systematic measurement error that can be caused, for example, by the presence of $O_2$ occurs when determining the concentration of $NO_x$. It has been shown that the CLD method that has proven effective for low $NO_x$ concentrations exhibits systematic deviations for high $O_2$ and $NO_x$ concentrations. The method according to the invention thus determines a measurement value for the $NO_x$ concentration and a numerical value for the $NO_x$ concentration, wherein the numerical value can be used as a corrected measurement value or as a difference or factor for a corrected measurement value. Alternatively or additionally, as the second component an oxygen compound, for example, $CO_2$, could be used. Here, for example, the $O_2$ percentage can be determined indirectly via the $CO_2$ percentage and the λ value of the measurement gas or the direct influence of $CO_2$ on the $NO_x$ concentration determined with a specified measurement method is taken into consideration.

According to one construction of the invention, it could be provided that the measurement value and the numerical value for the $NO_x$ concentration in the measurement gas are displayed. Thus, the user of the method can decide for himself which of the two displayed values he wants to use for his actual application, wherein the numerical value can be a corrected measurement value or a difference value that is to be added to the measurement value or subtracted from this measurement value or a factor with which the measurement value is to be multiplied.

For monitoring regulations for combustion engines, it can be provided that the measurement gas is taken from the exhaust gases of a combustion engine, for example, of a diesel engine. Here it is advantageous that the method can also be used when the exhaust gas has a high $O_2$ percentage.

The determination of the concentration of the second component in the measurement gas can be carried out by a separate analysis method or by some other input of the relevant values. For an automated execution of the method according to the invention, however, it is advantageous when a second gas sensor is provided for the determination of the concentration of the other component in the measurement gas.

For determining the measurement value for the $NO_x$ concentration from the sensor signal of the gas sensor it can be provided that the measurement value for the $NO_x$ concentration in the measurement gas is determined with reference to a stored first characteristic line from the sensor signal of the first gas sensor.

Alternatively or additionally it could be provided that the numerical value for the $NO_x$ concentration in the measurement gas is determined with reference to a stored second characteristic line from the sensor signal of the first and/or second gas sensor. Thus, the numerical value for the $NO_x$ concentration can be determined as a corrected measurement value as a function of the first and second sensor signal and/or as a difference value for the measurement value determined with the first gas sensor for the $NO_x$ concentration from the sensor signal of the second gas sensor.

An especially simple determination of the measurement values or numerical values is produced when the first characteristic line and/or the second characteristic line is/are formed by interpolation or extrapolation of calibration or support points each of a characteristic line curve. In this way it is advantageously achieved that for setting up the method according to the invention, the recording of only a small number of calibration points is required. The characteristic lines are advantageously defined and/or determined by calibration and/or comparison measurements.

For achieving an improved measurement accuracy, it can be provided that the first characteristic line and/or the second characteristic line is/are stored as data series, that is, with a plurality of measurement points. This is especially advantageous when, for an interpolation or extrapolation based on the specific properties of the gas-sensor type being used, undesired deviations and/or systematic errors are to be expected.

According to one advantageous embodiment of the invention, it can be provided that the first characteristic line is the characteristic line of an electrochemical sensor, an infrared sensor, a UV sensor, or a semiconductor sensor, and that the second characteristic line maps the deviations of a chemiluminescence detector from the first characteristic line for different values of concentration of the other component in the measurement gas. Tests have shown that infrared sensors, UV sensors, or electrochemical sensors that advantageously have constructions sensitive to $NO_x$ exhibit a measurement response deviating from frequently specified chemiluminescence detectors for a high $O_2$ percentage in the measurement gas, in which an undesired systematic error source is eliminated or at least reduced. Instead of the electrochemical sensors, semiconductor sensors could also be used.

According to another advantageous embodiment, it could be provided that the first characteristic line is the characteristic line of a chemiluminescence detector and that the second characteristic line maps the deviations of the characteristic line of an electrochemical sensor, an infrared sensor, ITV sensor, or semiconductor sensor from the first characteristic line for different values of the concentration of the other component in the measurement gas. In this way it is advantageously achieved that even for the use of a chemiluminescence detector that is frequently specified legally or for other reasons, corrected measurement values for the $NO_x$ concentration that take into consideration the described systematic errors can be provided with the method according to the invention.

The infrared sensor is advantageously constructed as a non-dispersive IR sensor. The CLD sensor is advantageously constructed sensitive to $NO_x$.

One especially advantageous construction is produced when an electrochemical sensor is used for the first characteristic line or for the second characteristic line.

For a simplified monitoring of the legal regulations it can be provided that the exceeding and/or falling below of limit values for the measurement value and/or numerical value for the $NO_x$ concentration in the measurement gas are signaled separately. The signaling can be realized optically, acoustically, or by printout in a log or in some other way. Thus, the user can advantageously limit himself to information on the $NO_x$ concentration corrected by systematic errors, while the method according to the invention ensures that the exceeding and/or falling below of limit values that are specified legally or for some other reasons is signaled independent of this limitation.

For example, for a construction of the method according to the invention it can be provided that the difference between measurement value and numerical value for the $NO_x$ concentration in the measurement gas increases or decreases with increasing concentration of the second component in the measurement gas.

A further improved method is given in that at least one additional measurement and/or characteristic value for the concentration of an additional component in the measurement gas is calculated and/or input and that a correction value for the $NO_x$ concentration in the measurement gas is determined from the additional measurement and/or characteristic value. For example, it could be provided that through the concentration of the additional component in the measurement gas, the moisture content in the measurement gas is determined, especially the additional component is water or water vapor. Alternatively or additionally, it could be provided that the additional component is $CO_2$. Through the consideration of additional components, systematic errors due to the presence of additional components are taken into account even better or the influence of the moisture content on the measurement value is taken into account. The determination of the at least one component is carried out, for example, by a correspondingly constructed gas sensor.

For the further improvement of the method it can be provided that the determination of the numerical value for the $NO_x$ concentration in the measurement gas from the measurement value for the concentration of the second component and/or the additional component is carried out as a function of the moisture content of the measurement gas. The moisture content of the measurement gas can be carried out here, for example, by the input of a numerical value and/or by the input of a dew point in the measurement gas and/or by a measurement on the measurement gas, for example, with a $ZrO_2$ probe. Tests have shown that the influence of the moisture content in the measurement gas is considerable when increased requirements are placed on the measurement accuracy, because oxygen can dissolve in the water contained in the measurement gas, wherein a correction of cross-sensitivities to other substances is advantageous more than ever. For a simple realization, it can be provided that the moisture content of the measurement gas is taken into account only in steps, for example, in two, three, or more than three steps.

For the use of a gas dehydration unit, for example, a gas cooler connected before the gas sensor, the consideration of the moisture content in the measurement gas is required when the $NO_x$ concentration for moist measurement gas is to be calculated. Conversely, the moisture content could be used to calculate a $NO_x$ concentration for dried measurement gas for a measurement without gas dehydration.

If the measurement gas involves the exhaust gas of a combustion engine, the moisture content could also be calculated from the parameters of the chemical substances fed to the combustion engine, especially the fuel and/or the air, and from the combustion products. Alternatively, in this way, the moisture content could also be measured directly.

For taking into account the moisture content of the measurement gas, here it could be provided that, for the fed chemical substances, elementary components, in particular, H and/or C, can be determined by means of an elementary analysis and/or the moisture content of the measurement gas is calculated, in particular, from the determined elementary components. Advantageously, in the elementary analysis, concentrations of the elementary components are determined from which the moisture content can be calculated. Alternatively or additionally, the moisture content of the air fed to the combustion engine can be determined.

For meeting the objective and especially for carrying out the method according to the invention, for a device for determining a $NO_x$ concentration in a measurement gas that has a gas sensor that is sensitive for $NO_x$ and can be brought into contact with the measurement gas and an evaluation unit for determining a measurement value for the $NO_x$ concentration in the measurement gas from the sensor signal of the gas sensor it is provided that an additional gas sensor is provided that is constructed for determining the concentration of a second component in the measurement gas and that the evaluation unit has means for determining a numerical value for the $NO_x$ concentration in the measurement gas from the measurement value determined with the first gas sensor for the NO concentration in the measurement gas and in the sensor signal of the second gas sensor. Advantageously, means for carrying out the described method according to the invention are constructed in the device.

In one advantageous construction it can be provided that the device has a portable construction, for example, in that the components of the device are arranged in a common housing.

According to one construction of the invention it can be provided that a storage means is provided in or on the device, wherein a first characteristic line for the evaluation of the sensor signal of the first gas sensor and a second characteristic line for the evaluation of the second sensor signal are stored in this storage means, wherein a difference value by which the numerical value deviates from the measurement value for the $NO_x$ concentration in the measurement gas or a factor with which the measurement value for the $NO_x$ concentration is to be multiplied for determining a corrected measurement value, that is, the numerical value can be inferred from the second characteristic line. Thus, the correction of systematic measurement errors due to the influences by the second component or the simulation of a measurement method that is legally specified or already established can be carried out in an especially easy way and the device according to the invention can be easily adapted to changing legal regulations or the selection of a different reference method. The stored characteristic lines are advantageously obtained through reference measurements and stored as data series and/or as functional dependencies in a memory.

In one refinement, different characteristic lines are stored for different reference measurement methods, so that for a plurality of measurement methods the appropriate resulting measurement value can be assigned for the NO concentration. For simplification, a characteristic line or its parameters averaged across different measurement methods could also be stored.

For achieving an improved consideration of the influences caused by additional components of the measurement gas it can be provided that means for the input and/or determination of the concentration of an additional component in the measurement gas are constructed and that, for different numerical values of this concentration of the additional component, different characteristic lines are stored from each of which the difference value or factor by which the numerical value deviates from the measurement value for the $NO_x$ concentration in the measurement gas can be inferred. This difference value or factor can be given for the invention, in general, in that the measurement value achieved with the measurement method and the numerical value corrected by systematic measurement errors are stored, wherein the difference is produced by the formation of a difference or that a factor is stored with which the measurement value is to be multiplied, in order to achieve the corrected measurement value, wherein the factor is produced by the formation of a quotient, or that the difference value or the factor is stored directly. For many application requirements, it is already sufficient if the input of the concentration of an additional component in the measurement gas is allowed in discrete steps. For example, the additional component could be the water content in the measurement gas and thus the moisture content of the measurement gas.

In one construction of the invention it can be provided that a gas cooler 25 and/or a condensate trap 26 in the gas flow of the measurement gas is arranged before the gas sensor 22 or the gas sensors 22, 23. Here it is advantageous that a defined moisture content of the measurement gas is set by the upstream gas cooler 25 or the upstream condensate trap 26, wherein systematic measurement errors are reduced.

For the consideration of the influence of the moisture content in the measurement gas it can be provided that means for the identification 27 of the presence of a gas cooler 25 or a condensate trap 26 in the gas flow of the measurement gas and/or means for the identification and/or input of the operating temperature of the gas cooler or the condensate trap are provided. Through these means, a conclusion on the moisture content that can be used for the correction of systematic measurement errors is possible in the measurement gas at least in coarse steps.

For determining the moisture content in the measurement gas, a moisture sensor, for example, a $ZrO_2$ probe could be brought into contact with the measurement gas before the gas cooler or, in general, a gas dehydration device or instead of the gas dehydration device. With the measurement values for the moisture, the corrected measurement values for the $NO_x$ concentration in dry measurement gas can be converted to moist measurement gas and vice versa.

If the device according to the invention is used for determining the $NO_x$ percentage in the exhaust gas of a combustion engine, then sensors and/or input means could be provided for determining the moisture content, wherein parameters of the fuel being used, for example, the H or C percentage, and of the fed air, for example, the $O_2$ percentage, could be calculated or input with these sensors or input means. In this case, means that allow a calculation of the moisture content in the exhaust gas from these parameters are constructed on the device.

BRIEF DESCRIPTION OF THE DRAWINGS

The invention will now be described with reference to embodiments, but is not limited to these embodiments. Additional embodiments are given through the combination of features of the claims with each other and/or with features of the embodiments.

Shown are.

DETAILED DESCRIPTION OF THE PREFERRED EMBODIMENTS

Figure 1:
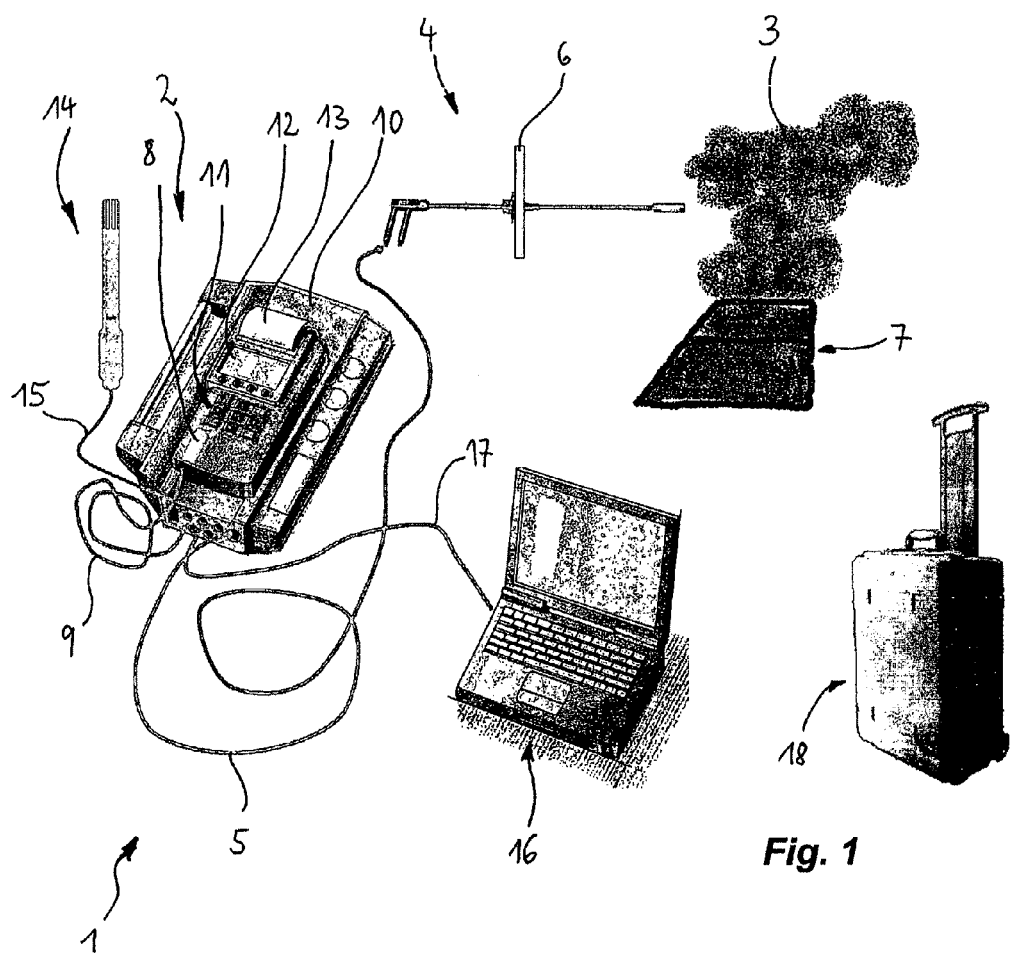
FIG. 1: an arrangement according to the invention for determining the NOx concentration in the exhaust gas of an engine.

FIG. 1 shows a sketched principle configuration of a general arrangement designated with 1 with a device 2 for determining a $NO_x$ concentration in a measurement gas 3.

The arrangement here has a probe 4 with which a portion of the measurement gas 3 can be extracted and fed via an unheated hose 5 to the device 2. The feeding of the measurement gas 3 via the hose 5 is carried out as described in DE 196 31 002 C2, in particular, on Page 3, Line 29 to Page 4, Line 10 and in the patent claims of this publication.

In another embodiment, the hose 5 can be heated.

For extracting the measurement gas sample in FIG. 1, the probe 4 is attached with its fastening flange 6 to the flue 7 from which the measurement gas 3 is extracted.

The device 2 is equipped according to the requirements for determining the concentration of $O_2$, CO, NO, $NO_2$, and $SO_2$ with the help of electrochemical sensors and also has available a $CO_2$—IR sensor including absolute pressure measurement.

The device 2 has available an evaluation unit 8 with means for determining a numerical value for the NOx concentration in the measurement gas from the measurement value determined with the first gas sensor 22 for the NOx concentration in the measurement gas 3 and the sensor signal of the second gas sensor 23 for the $O_2$ concentration in the measurement gas 3.

The evaluation unit 8 is connected via a data line 9 to the base body 10 of the device 2 that encloses, forming a housing, the sensors for determining the concentrations of the components in the portion of the measurement gas 3 extracted via the probe 4.

On the evaluation unit 8 that can be separated from the base body 10 there are input means 11 for the input of control commands and/or numerical values, display means 12 for the display of control steps, input requirements, or measurement values and/or calculated numerical values, and output means 13 for the output of measurement logs and measurement values.

In the evaluation unit 8 there is a storage means 24 or memory in which a first characteristic line for the evaluation of the sensor signal of the NOx gas sensor 22 and a second characteristic line for the evaluation of the second sensor signal of the $O_2$ sensor 23 are stored.

Another measurement device 14 is connected via another data line 15 to the evaluation unit 8 for determining ambient moisture and ambient temperature.

For the further processing of the calculated measurement values and/or the measurement log, a PC 16 is connected via a connection line 17 to the evaluation unit 8. The components of the arrangement 1 can be stored in an accessories cabinet 18 for transport.

In the device 2 shown in FIG. 1, an electrochemical sensor is provided for determining the $NO_x$ component in the measurement gas 3 and a characteristic line is stored in the evaluation unit 8, wherein the sensor signal of the $O_2$ sensor can be evaluated with this characteristic line for the simulation of the measurement of the $NO_x$ concentration with a CLD sensor.

In another embodiment it can be provided that the evaluation unit 8 in FIG. 1 contains a CLD sensor for determining the $NO_x$ concentration and that a characteristic line is stored in the evaluation unit 8 for evaluating the sensor signal of the $O_2$ sensor with which the described measurement value deviation of the CLD sensor can be corrected for a high $O_2$ percentage in the measurement gas. In this embodiment, the hose 5 is heated for feeding the measurement gas and a gas cooler is provided for measurement on dry exhaust gas in the measurement gas flow and no gas cooler is provided for measurement on the moist exhaust gas in the measurement gas flow.

With the described arrangement, a method for determining a $NO_x$ concentration in the measurement gas 3 can be carried out that will be described in detail below.

In the evaluation unit 8, a sensor signal of a gas sensor is captured, wherein this sensor is arranged in the base body 10 and is sensitive to $NO_x$ and is brought into contact with the measurement gas 3 via the probe 4 and the hose 5.

From this detected sensor signal, a measurement value for the $NO_x$ concentration is then determined.

By means of an additional sensor in the base body 10 of the device 2, a measurement value for the concentration of $O_2$ in the measurement gas 3 is determined.

From the two determined measurement values for the concentration of $NO_x$ and $O_2$, a numerical value for the $NO_x$ concentration in the measurement gas 3 is now determined that would be produced for the use of a CLD sensor instead of the electrochemical sensor.

The measurement value measured with the electrochemical sensor for the $NO_x$ concentration in the measurement gas 3 and the determined numerical value that would be produced for the use of a CLD sensor are displayed on the display means 12 of the evaluation unit 8.

For determining the measurement values and numerical values, characteristic lines are stored in the evaluation unit 8.

The device 2 also has available, in the base body 10, a gas cooler that is not visible in the illustration and is connected before the gas sensors in the measurement gas flow. Thus, the gas sensors in the base body 10 measure the dry measurement gas flow. With the knowledge of the moisture content of the measurement gas 3 before entry into the gas cooler, the $NO_x$ concentration for moist measurement gas can be calculated from this knowledge.

In another embodiment, the gas cooler has a separate construction.

Figure 2:
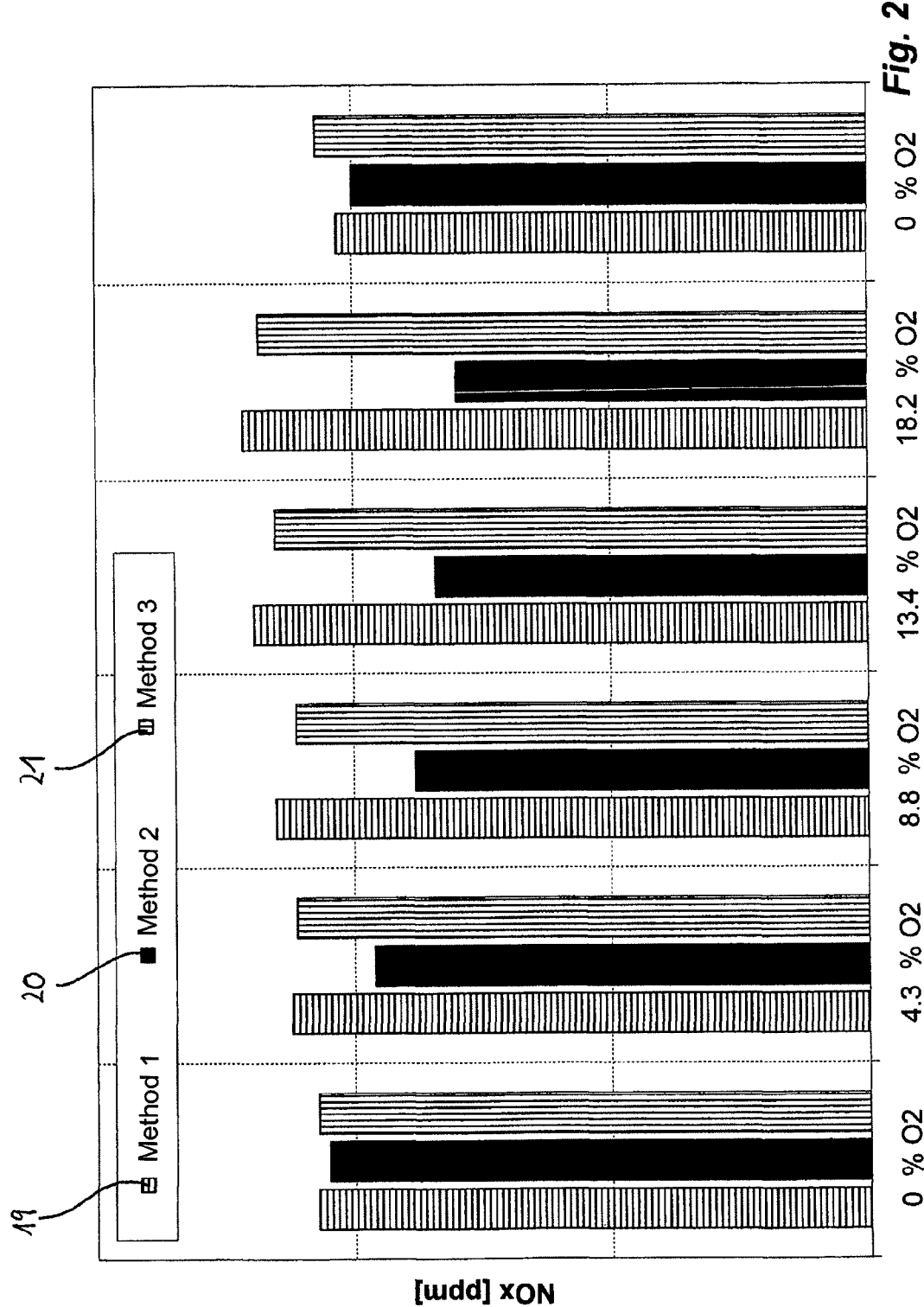
FIG. 2: the influence of the oxygen concentration on the NOx concentration determined with different measurement methods.
Figure 3:
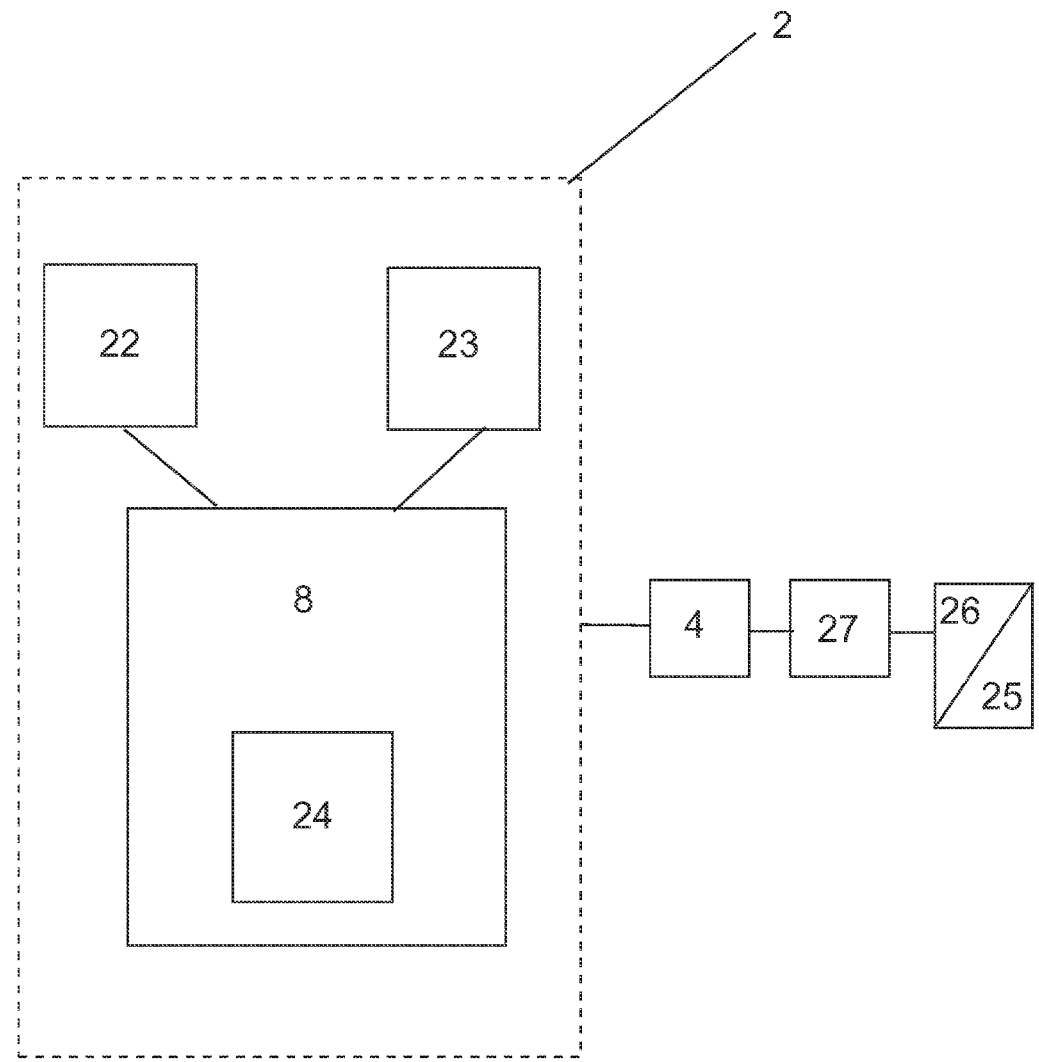
FIG. 3: a partial schematic representation of the device shown in the arrangement of FIG. 1.

FIG. 2 shows the result of a series of measurements in which the $NO_x$ concentration in a measurement gas was determined for different oxygen concentrations with different measurement methods. Shown are the determined $NO_x$ concentrations with a non-dispersive infrared sensor 19, with a chemiluminescence detector 20, and with an electrochemical sensor 21.

Here, the abscissa represents the values measured with the different methods for the $NO_x$ concentration at different oxygen concentrations in the measurement gas. Deviations with increasing oxygen content can be seen clearly.

It can be clearly seen that the measurement values achieved with the non-dispersive infrared sensor 19 agree with the measurement values achieved by means of the electrochemical sensor 21 in the scope of statistical deviations, while deviations to the measurement values 20 of the CLD sensor are produced that increase in magnitude with increasing oxygen content.

From this information, a characteristic line can be derived with which the $NO_x$ concentration determined from a CLD sensor can be corrected with knowledge of the $O_2$ concentration or with which the measurement with a CLD sensor can be simulated on the basis of a measurement of the $NO_x$ concentration with an IR or electrochemical sensor.

The mentioned information is stored in the form of characteristic lines in the evaluation unit 8 and is used for determining the numerical value for the $NO_x$ concentration that is displayed on the display means 12 and is optionally output with the output means 13.

In the evaluation unit 8, limit values specified legally or as a reference are stored for $NO_x$ concentrations and the exceeding and/or falling below of these limit values for each of the measurement value and the numerical value for the $NO_x$ concentration in the measurement gas is signaled separately on the display means 12 or logged in a measurement log. In the evaluation unit 8, for additional components, especially $CO_2$ and water, in the measurement gas 3 analogous to FIG. 2, the deviation of the different measurement methods from each other are stored, so that the influences caused by the additional components on the determination of the $NO_x$ concentration can be taken into account.

In the evaluation unit 8, the sensor signals of gas sensors are finally processed in the base body 10 such that a calculation of the moisture content of the measurement gas 3 is possible before entry into the gas cooler.

In the method for determining a $NO_x$ concentration in a measurement gas, it is provided that a measurement value for the $NO_x$ concentration is determined from the sensor signal of a gas sensor and that a measurement value for the concentration of a second component in the measurement gas is determined, wherein, a corrected value for the $NO_x$ concentration in the measurement gas is determined from the measurement values and wherein the measurement value and the corrected measurement value for the $NO_x$ concentration are displayed and/or output.

The invention claimed is:

1. Method for determining a $NO_x$ concentration in a measurement gas, comprising:
providing a sensor signal from a first gas sensor that is sensitive for $NO_x$ and that is brought into contact with the measurement gas and determining a measurement value for the $NO_x$ concentration from the sensor signal,
determining a measurement value for a concentration of a second component in the measurement gas from a second gas sensor, the second component being oxygen,
determining a numerical value for the $NO_x$ concentration in the measurement gas from the measurement value for the oxygen concentration in the measurement gas, and
displaying the measurement value and the numerical value for the $NO_x$ concentration in the measurement gas,
wherein the measurement value for the $NO_x$ concentration in the measurement gas is determined with reference to a stored first characteristic line from the sensor signal of the first gas sensor,
wherein the numerical value for the $NO_x$ concentration in the measurement gas is determined with reference to a stored second characteristic line from the sensor signal of at least one of the first or the second gas sensor.

2. Method according to claim 1, further comprising removing the measurement gas from exhaust gases of a combustion engine.

3. Method according to claim 1, wherein at least one of the first characteristic line (19, 20, 21) or the second characteristic line is formed by interpolation or extrapolation of calibration or support points each of a characteristic line curve.

4. Method according to claim 1, wherein at least one of the first characteristic line (19, 20, 21) or the second characteristic line is stored as a data series.

5. Method according to claim 1, wherein the first characteristic line (19, 20, 21) is the characteristic line of an infrared sensor, UV sensor, electrochemical sensor, or semiconductor sensor or a chemiluminescence detector.

6. Method according to claim 1, wherein the second characteristic line maps deviations of a characteristic line of a $NO_x$ sensitive electrochemical sensor, infrared sensor, UV sensor, or semiconductor sensor or a chemiluminescence detector from the first characteristic line for different values of a concentration of the second component in the measurement gas.

7. Method according to claim 1, further comprising separately signaling at least one of exceeding or falling below limit values for the measurement value and numerical value for the $NO_x$ concentration in the measurement gas.

8. Method according to claim 1, wherein a difference between the measurement value and numerical value for the $NO_x$ concentration in the measurement gas increases or decreases with increasing concentration of the second component in the measurement gas.

9. Method according to claim 1, wherein at least one additional measurement or characteristic value for a concentration of third component in the measurement gas is at least one of determined or input and a correction value for the $NO_x$ concentration in the measurement gas is determined from at least one of the additional measurement or characteristic value.

10. Method according to claim 9, wherein the third component is water and the determination of the numerical value for the $NO_x$ concentration in the measurement gas is carried out from the measurement value for the concentration of at least one of the second component or the third component as a function of a moisture content of the measurement gas.

11. Method according to claim 1, wherein the measurement gas is an exhaust gas of a combustion engine and for chemical substances fed to the combustion engine, a concentration of elementary components, including at least one of H or C, or a moisture content of air fed to the combustion engine are determined by an elementary analysis or the moisture content of the measurement gas is calculated from determined concentrations of the elementary components or a moisture content of air fed to the combustion engine.

12. Method according to claim 11, wherein the moisture content in the measurement gas is measured.

13. Device for determining a $NO_x$ concentration in a measurement gas, comprising:
a first gas sensor that is sensitive to $NO_x$ configured for contact with the measurement gas to produce a first sensor signal,
a second gas sensor sensitive to a second component of the measurement gas (3) configured for contact with the measurement gas to produce a second signal,
an evaluation unit (8) configured to determine a measurement value for the $NO_x$ concentration in the measurement gas (3) from the first sensor signal from the first gas sensor and a numerical value for the $NO_x$ concentration in the measurement gas from the measurement value determined from the first sensor signal and the second sensor signal,
a display that displays the numerical value and the measurement value, and
a storage device in which a first characteristic line for evaluation of the sensor signal of the first gas sensor and a second characteristic line for evaluation of a second sensor signal are stored,
wherein the evaluation unit determines a difference value or factor by which a numerical value deviates from the measurement value for the $NO_x$ concentration in the measurement gas using the second characteristic line,
wherein different characteristic lines are stored from which a difference value or factor can be taken by which the numerical value deviates from the measurement value for the $NO_x$ concentration in the measurement gas.

14. Device according to claim 13, further comprising a gas cooler or a condensate trap is arranged, upstream of the first or second gas sensor, in the gas flow of the measurement gas.

15. Device according to claim 14, further comprising an identification device, between the gas cooler or condensate trap and the first or second gas sensor, that identifies a presence of the gas cooler or the condensate trap in the gas flow of the measurement gas.

16. Device according to claim 14, further comprising an identification device, between the gas cooler or condensate trap and the first or second gas sensor, that allows identification or input of an operating temperature of the gas cooler or the condensate trap.

17. Device according to claim 14, further comprising an identification device, between the gas cooler or condensate trap and the first or second gas sensor, that determines the moisture content in the measurement gas.

18. Device according to claim 13, wherein the second gas sensor is an $O_2$ sensor.

19. Device according to claim 13, wherein the device (2) has a portable construction.

20. Method for determining a $NO_x$ concentration in a measurement gas, comprising:
providing a sensor signal from a first gas sensor that is sensitive for $NO_x$ and that is brought into contact with the measurement gas and determining a measurement value for the $NO_x$ concentration from the sensor signal, determining a measurement value for a concentration of a second component in the measurement gas from a second gas sensor, the second component being oxygen, determining a numerical value for the $NO_x$ concentration in the measurement gas from the measurement value for the oxygen concentration in the measurement gas, and displaying the measurement value and the numerical value for the $NO_x$ concentration in the measurement gas, wherein the measurement value for the $NO_x$ concentration in the measurement gas is determined with reference to a stored first characteristic line from the sensor signal of the first gas sensor, wherein the numerical value for the $NO_x$ concentration in the measurement gas is determined with reference to a stored second characteristic line from the sensor signal of at least one of the first or the second gas sensor and wherein the first characteristic line (19, 20, 21) is the characteristic line of: an infrared sensor, UV sensor, an electrochemical sensor, or a semiconductor sensor.

21. Method for determining a $NO_x$ concentration in a measurement gas, comprising:

providing a sensor signal from a first gas sensor that is sensitive for $NO_x$ and that is brought into contact with the measurement gas and determining a measurement value for the $NO_x$ concentration from the sensor signal, determining a measurement value for a concentration of a second component in the measurement gas from a second gas sensor, the second component being oxygen, determining a numerical value for the $NO_x$ concentration in the measurement gas from the measurement value for the oxygen concentration in the measurement gas, and displaying the measurement value and the numerical value for the $NO_x$ concentration in the measurement gas, wherein the measurement value for the $NO_x$ concentration in the measurement gas is determined with reference to a stored first characteristic line from the sensor signal of the first gas sensor, wherein the numerical value for the $NO_x$ concentration in the measurement gas is determined with reference to a stored second characteristic line from the sensor signal of at least one of the first or the second gas sensor and wherein the first characteristic line (19, 20, 21) is the characteristic line of a chemiluminescence detector.

* * * * *